US010736827B2

(12) United States Patent
Mueller et al.

(10) Patent No.: US 10,736,827 B2
(45) Date of Patent: Aug. 11, 2020

(54) HAIR DYE AGENT HAVING UNILAMELLAR AND MULTILAMELLAR VESICLES

(71) Applicant: Henkel AG & Co. KGaA, Duesseldorf (DE)

(72) Inventors: Burkhard Mueller, Duesseldorf (DE); Lucile Bonnin, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/324,456

(22) PCT Filed: Jun. 20, 2017

(86) PCT No.: PCT/EP2017/065084
§ 371 (c)(1),
(2) Date: Feb. 8, 2019

(87) PCT Pub. No.: WO2018/028861
PCT Pub. Date: Feb. 15, 2018

(65) Prior Publication Data
US 2019/0175459 A1    Jun. 13, 2019

(30) Foreign Application Priority Data
Aug. 9, 2016    (DE) .................. 10 2016 214 716

(51) Int. Cl.
| *A61Q 5/10* | (2006.01) |
| *A61K 8/14* | (2006.01) |
| *A61K 8/34* | (2006.01) |
| *A61K 8/37* | (2006.01) |
| *A61K 8/46* | (2006.01) |
| *A61K 8/06* | (2006.01) |
| *A61K 8/86* | (2006.01) |
| *A61K 8/38* | (2006.01) |
| *A61K 8/39* | (2006.01) |
| *A61K 8/49* | (2006.01) |
| *A61Q 5/08* | (2006.01) |
| *A61K 8/22* | (2006.01) |

(52) U.S. Cl.
CPC ............... *A61K 8/14* (2013.01); *A61K 8/068* (2013.01); *A61K 8/22* (2013.01); *A61K 8/342* (2013.01); *A61K 8/375* (2013.01); *A61K 8/38* (2013.01); *A61K 8/39* (2013.01); *A61K 8/463* (2013.01); *A61K 8/4906* (2013.01); *A61K 8/86* (2013.01); *A61Q 5/08* (2013.01); *A61Q 5/10* (2013.01); *A61K 2800/21* (2013.01); *A61K 2800/30* (2013.01); *A61K 2800/596* (2013.01); *A61K 2800/805* (2013.01); *A61K 2800/88* (2013.01)

(58) Field of Classification Search
CPC .. A61Q 5/10; A61K 8/342; A61K 2800/4324; A61K 8/86; A61K 8/39; A61K 8/345; A61K 8/463; A61K 8/375; A61K 8/06; A61K 2800/596; A61K 2800/88; A61K 8/14; A61K 8/22; A61K 8/38; A61K 8/068; A61K 2800/21
See application file for complete search history.

(56) References Cited

U.S. PATENT DOCUMENTS

| 6,616,706 | B1 | 9/2003 | Kahre et al. | |
| 8,858,653 | B2 | 10/2014 | Schettiger et al. | |
| 10,045,924 | B2 | 8/2018 | Neuba et al. | |
| 2005/0283925 | A1* | 12/2005 | Glenn | A61K 8/411 8/405 |
| 2012/0325244 | A1* | 12/2012 | Hashimoto | A61Q 5/10 132/208 |
| 2015/0335563 | A1* | 11/2015 | Allard | A61K 8/31 8/406 |

FOREIGN PATENT DOCUMENTS

| DE | 102005053349 A1 | 5/2007 |
| DE | 102014226321 A1 | 6/2016 |
| DE | 102015222985 A1 | 7/2016 |
| EP | 1433475 A1 | 6/2004 |
| EP | 1761235 B1 | 3/2007 |
| WO | 2015112787 A1 | 7/2015 |

OTHER PUBLICATIONS

STIC Search Report dated Oct. 17, 2019.*
EPO, International Search Report and Written Opinion issued in International Application No. PCT/EP2017/065084, dated Aug. 7, 2017.

* cited by examiner

*Primary Examiner* — Eisa B Elhilo
(74) *Attorney, Agent, or Firm* — Lorenz & Kopf, LLP

(57) ABSTRACT

The present disclosure relates to an agent (A) for changing the colour of keratin fibres, in particular human hair, which agent comprises unilamellar vesicles (ULV) and/or multilamellar vesicles (MLV) in an aqueous medium, wherein the agent contains at least one $C_8$-$C_{30}$ fatty alcohol (a1), at least one ethoxylated fatty alcohol (a2), at least one anionic surfactant of the type of (optionally ethoxylated) fatty alcohol sulfates (a3), and one or more colour-changing salts (a4) from the group of sulfates, hydrogen sulfates, chlorides, and/or bromides in a total amount of from about 0.3 to about 6.0% by weight.
The present disclosure further relates to a multi-component packaging unit, in which the aforementioned agent (A) is formulated separate from an oxidant preparation (B). The present disclosure further relates to a method for producing the agent (A).

20 Claims, No Drawings

HAIR DYE AGENT HAVING UNILAMELLAR AND MULTILAMELLAR VESICLES

CROSS-REFERENCE TO RELATED APPLICATION

This application is a U.S. National-Stage entry under 35 U.S.C. § 371 based on International Application No. PCT/EP2017/065084, filed Jun. 20, 2017, which was published under PCT Article 21(2) and which claims priority to German Application No. 10 2016 214 716.1, filed Aug. 9, 2016, which are all hereby incorporated in their entirety by reference.

TECHNICAL FIELD

The present disclosure lies in the field of cosmetics. The present disclosure relates to agents (A) for changing the colour of keratin fibres, which agents comprise unilamellar vesicles (ULV) and/or multilamellar vesicles (MLV) in an aqueous medium, and furthermore at least one fatty alcohol, at least one ethoxylated fatty alcohol, at least one anionic surfactant, and specific amount ranges of colour-changing compounds in salt form.

The present disclosure further relates to a multi-component packaging unit, in which the aforementioned agent (A) is formulated separate from an oxidant preparation (B). The present disclosure thirdly relates to a method for producing the agent (A).

BACKGROUND

The use of emulsions is widespread in cosmetics. An emulsion comprises a finely dispersed mixture of two liquids, such as fat bodies (oils, fatty alcohols, hydrocarbons or also fatty acid triglycerides) and water. One theory regarding emulsions is that one of the liquids (phase) forms small droplets which are present dispersed in the other liquid (phase). The phase that forms the droplets is referred to as the inner phase or also disperse phase. The phase in which the droplets float is called the outer phase or also the continuous phase.

In the case of emulsions that comprise a water phase and an oil phase, a distinction is made between oil-in-water emulsions (O/W emulsions) and water-in-oil emulsions (W/O emulsions). Classic O/W emulsions are described in the literature often as oil droplets which are dispersed in the continuous water phase and are stabilised at the interface of both phases by surfactants or emulsifiers. The latter form a film around the oil droplets and are thus able to reduce the surface tension. In complex cosmetic formulations, however, a number of various ingredients are generally used, thus resulting in complex multiphase systems.

In the field of hair dye agents and hair bleaching agents, the use of formulations that are based on high amounts of fatty alcohols (fatty amphiphiles) and surfactants is known. Lamellar networks, which are also described as lamellar gel networks or multilamellar structures, are often created in formulations of this type.

WO 2015/112787 A1 describes hair dyes that comprise a multilamellar emulsion and that, in addition to colouring substances, also contain a combination of polar nonionic surfactants and nonionic surfactants that are less polar.

EP 1 433 475 A1 relates to hair dye agents which, besides ammonia and oxidation dyes, also contain at least about 10% by weight of a mesomorphic phase, wherein the term "mesomorphic phases" also includes lamellar phases.

EP 1 761 235 B1 lastly claims dye agents which contain the oxidation dye precursors encapsulated in or adsorbed on multilamellar vesicles.

The dye agents described in these documents, however, cannot yet be considered optimal in respect of their application properties, in particular in respect of their stability.

In order to produce permanent, intense colourations with corresponding fastness properties, what are known as oxidation dyes are used. Such dyes usually contain oxidation dye precursors, or what are known as developer components and coupler components. The developer components form the actual colouring agent under the influence of oxidants or atmospheric oxygen, either on their own or with coupling to one or more coupler components. The oxidation dyes are exemplified by intense, outstanding, long-lasting colour results. A mixture of a greater number of oxidation dye precursors can be used for naturally acting colouring agents, wherein substantive dyes are also used additionally in many cases to provide further colour shades.

Oxidation dye precursors of the developer type are based typically on the basic structure of p-phenylenediamine, p-aminophenol, or heterocyclic di- or polyamino compounds. Substances of this type are extremely sensitive to atmospheric oxygen and are usually used in the form of their physiologically acceptable salts for stabilisation, i.e. the amino groups provided in the substances are converted—wholly or partially—into the amino groups present in the substances and are neutralised by counterions (chlorides, bromides, hydrogen sulfates or also sulfates). If a user wishes to colour their hair in a particularly dark hue, for example a dark brown or black shade, said user will thus use a corresponding dye agent with a particularly high colourant content. Due to the high content of oxidation dye precursors, the corresponding salt content in these agents is also very high.

Emulsions, such as O/W emulsions, often react very sensitively to an increase of their salt content. The risk that an emulsion or a dye agent will separate and prove unstable under storage is therefore particularly high in the case of shades having a high colourant content.

BRIEF SUMMARY

Hair dyeing agents, multi-component packaging units, and methods for producing dyeing agents are provided herein. In an embodiment, an agent for changing the colour of keratin fibres is provided. The agent includes unilamellar vesicles and/or multilamellar vesicles in an aqueous medium. The agent includes (a1) at least one $C_8$-$C_{30}$ fatty alcohol, and (a2) at least one ethoxylated fatty alcohol of formula (I),

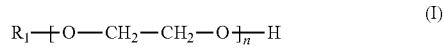

(I)

in which
R1 stands for a linear or branched, saturated or unsaturated $C_8$-$C_{30}$ alkyl group and
n stands for an integer from about 10 to about 100
The agent further includes (a3) at least one anionic surfactant of formula (II)

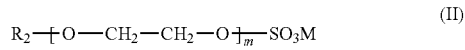

(II)

in which

R2 stands for a linear or branched, saturated or unsaturated $C_8$-$C_{30}$ alkyl group, m stands for an integer from 0 to about 10, and M stands for a hydrogen atom, an equivalent of a sodium ion, a potassium ion, or an ammonium ion ($NH_4^+$).

The agent further includes (a4) one or more colour-changing salts chosen from the group of sulfates, hydrogen sulfates, chlorides and/or bromides in a total amount of from about 0.3 to about 6.0% by weight, wherein the total amount relates to the total weight of the agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The first object of the present disclosure was therefore to provide dye agents that have an improved salt tolerance. In addition, the storage stability with high salt content should also be improved.

The fundamental precondition here was that the dye agents should demonstrate the above-mentioned improvements in respect of their salt tolerance without suffering any losses in respect of the further application properties. The colour intensity, washing fastness, and light fastness of these agents therefore should not deteriorate compared to the agents known from the prior art and, optimally, should be improved further.

It has now been found, surprisingly, that colour-changing salts in a total amount of up to about 6.0% by weight can be incorporated in a dye agent in a stable manner over a long period of time if said dye agent comprises unilamellar and/or multilamellar vesicles in an aqueous medium, and if the lamellar system in which the vesicles are located additionally contains fatty alcohols, ethoxylated fatty alcohols of a formula (I) and anionic surfactants of a formula (II). In spite of the high salt content, these vesicle-containing systems have proven to be particularly stable under storage, and intense colourations with good fastness properties could be obtained with their use. The stability of these vesicle systems in respect of temperature fluctuations was excellent.

A first subject of the present disclosure is an agent (A) for changing the colour of keratin fibres, in particular human hair, which agent comprises unilamellar vesicles (ULV) and/or multilamellar vesicles (MLV) in an aqueous medium, wherein the agent contains (a1) at least one $C_8$-$C_{30}$ fatty alcohol (a2) at least one ethoxylated fatty alcohol of formula (I),

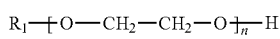 (I)

in which

R1 stands for a linear or branched, saturated or unsaturated $C_8$-$C_{30}$ alkyl group and n stands for an integer from about 10 to about 100

(a3) at least one anionic surfactant of formula (II)

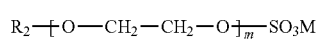 (II)

in which

R2 stands for a linear or branched, saturated or unsaturated $C_8$-$C_{30}$ alkyl group, m stands for an integer from about 0 to about 10, and M stands for a hydrogen atom, an equivalent of a sodium ion, a potassium ion, or an ammonium ion ($NH_4^+$), (a4) stands for one or more colour-changing salts from the group of sulfates, hydrogen sulfates, chlorides and/or bromides in a total amount of from about 0.3 to about 6.0% by weight, wherein the total amount relates to the total weight of the agent (A).

Keratin Fibres

The agent (A) is an agent for changing the colour of keratin fibres, in particular human hair. The agent (A) is particularly preferably used for the oxidative dyeing of keratin fibres, in particular human hair.

Keratin fibres are understood to mean wools, furs, feathers and in particular human hair. The agents as contemplated herein for oxidative changing of colour, however, can also be used in principle for changing the colour of other natural fibres, such as cotton, jute, sisal, flax or silk, modified natural fibres, such as regenerated cellulose, or nitro-, alkyl- or hydroxyalkyl- or acetylcellulose.

Unilamellar and/or Multilamellar Vesicles

The agents as contemplated herein comprise or contain unilamellar vesicles (ULV) and/or multilamellar vesicles (MLV) in an aqueous medium.

Vesicles are spherically lamellar, polydisperse amphiphilic structures of vesicle formers which are arranged in at least one double layer. These double layers contains, as vesicle formers as contemplated herein, fatty alcohols (a1), specific nonionic surfactants (a2), and specific anionic surfactants (a3).

Vesicles can be present as unilamellar vesicles (ULV) and multilamellar vesicles (MLV).

In unilamellar vesicles a double layer formed of vesicle formers (for example fatty alcohols and surfactants) encases a hydrophilic, water-containing interior. Multilamellar vesicles usually include a plurality of vesicles surrounding one another spherically, wherein the double membranes of these vesicles surrounding one another are arranged in a manner similar to layers of onion skin.

Unilamellar vesicles comprise a single spherical double membrane and, depending on diameter, are referred to as SULV (small unilamellar vesicle, maximum diameter about 50 nm (nanometres)) or LULV (large unilamellar vesicle, diameter greater than about 50 nm (nanometres)). The diameter of multilamellar vesicles is generally greater and lies in the range of about 100 nm (nanometres) to a few micrometres.

The active substances of the cosmetic dye agent (in particular the oxidation dye precursors present in salt form and/or the substantive dyes) can be located within the water-containing interior of the vesicle or also outside the vesicle and in this case as appropriate are in equilibrium with the active substances absorbed at the surface of the vesicle membrane.

The agents as contemplated herein comprise or contain unilamellar vesicles (ULV) and/or multilamellar vesicles (MLV) in an aqueous medium. Agents which contain multilamellar vesicles (MLV) have proven to be very particularly stable.

In a particularly preferred embodiment an agent (A) as contemplated herein comprises multilamellar vesicles (MLV).

Polarisation Microscopy

The presence of vesicles can be detected by employing polarisation microscopy. A polarisation microscope is a light microscope that uses polarised light for imaging. It is used for the examination of optically anisotropic objects.

In addition to a normal light microscope, a polarisation microscope contains two polarisers and an object stage, which is usually rotatable. Polarisation microscopes usually work in transmitted light mode, although reflected-light polarisation microscopes also exist. In the case of transmitted-light polarisation microscopes a polariser, also referred to as a polariser or primary filter, is disposed beneath the object stage and linearly polarises the light of the light source of the microscope, i.e. only allows through light that vibrates in a plane of oscillation. This direction of oscillation is oriented parallel to the polariser. A second polariser is disposed above the object stage and is referred to as an analyser or secondary filter and is rotated through 90° relative to the first filter. The direction of oscillation of the previously linearly polarised light is thus oriented exactly so that it is completely blocked by the analyser. It has no components that vibrate in the analyser direction, and therefore the image appears black. The arrangement of primary and secondary filter is referred to as "crossed polarisers".

If a specimen is located on the object stage between the two polarisers, the optical conditions may thus change. Some chemical compounds, for example minerals, have, under certain conditions, the property of rotating the plane of oscillation of the light and are referred to as birefringent or optically anisotropic. By changing the plane of polarisation, there is no longer complete cancellation—some of the light passes through the analyser and corresponding structures are visible. It is also possible to monitor any colours occurring as a result of interference. Optically isotropic materials, by contrast, remain dark.

The presence of vesicles, in particular multilamellar vesicles (MLV), can be detected by inspecting a specimen of the agent (A) by a polarisation microscope, for example with 400× magnification. The agent (A) is preferably examined under the polarisation microscope 24 hours after its production.

Since the vesicles, in particular the multilamellar vesicles, represent optically anisotropic structures, specially formed, light cross-shaped areas can be observed with the presence of vesicles and are also referred to as "Maltese cross patterns".

For example, a microscope from Zeiss (Axio Scope A2) with various lenses and with polariser can be used as polarisation microscope.

If, when examining a specimen under the polarisation microscope, Maltese crosses measuring from about 1 to about 20 μm (micrometres) in size are observed, the specific Maltese cross pattern can suggest the presence of multilamellar vesicles.

Diameter of the Unilamellar and Multilamellar Vesicles

Unilamellar and multilamellar vesicles differ in particular by their diameter.

Multilamellar vesicles usually have a diameter of about 100 nm (nanometres) up to about 6 μm (micrometres), preferably from about 100 nm (nanometres) up to about 2 μm (micrometres). Unilamellar vesicles by contrast have a smaller diameter of approximately 50 nm (nanometres) to typically approximately 100 nm.

During the course of the works leading to this present disclosure it was observed that agents (A) as contemplated herein which contained multilamellar vesicles (MLV) demonstrated a particularly high salt tolerance and a particularly good stability. Without being bound to this theory, it is assumed that the reason for these improved properties lies in the greater diameter of the vesicles. The greater diameter of the multilamellar vesicles (MLV) appears to be responsible for an increase in the viscosity of the agent, which in turn has a positive influence on the stability of the agent.

It has proven to be particularly preferred if the multilamellar vesicles have a mean diameter from about 0.2 to about 6.0 μm (micrometres), preferably from about 0.2 to about 2.0 μm (micrometres).

In a particularly preferred embodiment an agent (A) as contemplated herein comprises multilamellar vesicles (MLV) having a mean diameter from about 0.02 to about 6.0 μm (micrometres), preferably from about 0.2 to about 2.0 μm (micrometres).

The vesicle diameter in the sense of the present disclosure shall be understood to mean the mean vesicle diameter.

The mean diameter of vesicles can be measured as contemplated herein by employing dynamic light scattering. Dynamic light scattering is a method in which the scattered light of a laser is analysed at a dissolved or suspended specimen in order to determine the hydrodynamic radius of the molecules (or in the present case the vesicles). The dynamic light scattering is also known under the name photon correlation spectroscopy or quasi-electric light scattering. This method is suitable in particular in the case of vesicle diameters of up to about 2 μm (micrometres).

For example, a goniometer can be used for the measurement of the dynamic light scattering. Here, the laser unit is located on a stationary arm and the detector is located on a pivotable arm, usually an electron multiplier (EM) or an avalanche photodiode (APD). The measurement cell is located in the middle of the arrangement. The measurement can be carried out for example using the Zetasizer Nano ZS device from the company Malvern.

$C_8$-$C_{30}$ Fatty Alcohols

The presence of at least one $C_8$-$C_{30}$ fatty alcohol (a1) is essential for forming the vesicles. The agents as contemplated herein therefore contain one or more $C_8$-$C_{30}$ fatty alcohols as essential ingredient (a1). The $C_8$-$C_{30}$ fatty alcohols can be saturated, mono- or polyunsaturated, linear or branched fatty alcohols with from about 8 to about 30 C atoms.

Examples of preferred linear saturated $C_8$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear, unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidonic alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

In a particularly preferred embodiment the agent as contemplated herein contains at least one linear saturated $C_8$-$C_{30}$ fatty alcohol. The linear saturated $C_8$-$C_{30}$ fatty alcohols are particularly preferably used in the agent (A) as contemplated herein.

Particularly stable agents are obtained if they contain—in relation to their total weight—(a1) one or more linear, saturated $C_8$-$C_{30}$ fatty alcohols in a total amount from about 5.0 to about 25.0% by weight, preferably from about 7.0 to about 20.0% by weight, more preferably from about 10.0 to about 18.0% by weight, and particularly preferably from about 12.0 to about 16.0% by weight.

In a particularly preferred embodiment an agent (A) as contemplated herein contains—in relation to the total weight of the agent (A)—(a1) one or more linear, saturated $C_8$-$C_{30}$ fatty alcohols in a total amount from about 5.0 to about 25.0% by weight, preferably from about 7.0 to about 20.0% by weight, more preferably from about 10.0 to about 18.0% by weight, and particularly preferably from about 12.0 to about 16.0% by weight.

It has also been found that the stability and salt tolerance of the formulations can be improved further still if the agents as contemplated herein contain at least one branched $C_8$-$C_{30}$ fatty alcohol. The branched fatty alcohols are also preferably used in the agent as contemplated herein in specific amount ranges ranging from about 1.0 to about 9.0% by weight, preferably from about 1.3 to about 7.0% by weight, more preferably from about 1.6 to about 5.0% by weight, and particularly preferably from about 1.9 to about 3.0% by weight. Here, all amounts in % by weight relate to the total amount of the branched $C_8$-$C_{30}$ fatty alcohols used in the agent, which is set in relation to the total weight of the agent (A).

In a particularly preferred embodiment an agent (A) as contemplated herein contains—in relation to the total weight of the agent (A)—(a1) one or more branched, saturated $C_8$-$C_{30}$ fatty alcohols in a total amount from about 1.0 to about 9.0% by weight, preferably from about 1.3 to about 7.0% by weight, more preferably from about 1.6 to about 5.0% by weight, and particularly preferably from about 1.9 to about 3.0% by weight.

In a particularly preferred embodiment an agent (A) as contemplated herein contains—in relation to the total weight of the agent (A)—(a1) from about 1.0 to about 9.0% by weight, preferably from about 1.3 to about 7.0% by weight, more preferably from about 1.6 to about 5.0% by weight, and particularly preferably from about 1.9 to about 3.0% by weight 2-octyldodecanol.

In one embodiment the agent (A) as contemplated herein can contain linear, saturated $C_8$-$C_{30}$ fatty alcohols or branched saturated $C_8$-$C_{30}$ fatty alcohols. With regard to the stability of the agent (A), however, it has proven to be very particularly advantageous if the agent (A) contains both linear, saturated $C_8$-$C_{30}$ fatty alcohols and branched saturated $C_8$-$C_{30}$ fatty alcohols.

For example, the dye agents (A) which contained not only up to about 6% by weight of colour-changing salts, but also about 13.0% by weight cetearyl alcohol and about 2.0% by weight 2-octyldodecanol have thus proven to be extremely stable under storage.

Within the scope of a further embodiment, an agent (A) for changing the colour of keratin fibres, in particular human hair, that has proven to be very particularly preferred is one which comprises unilamellar vesicles (ULV) and/or multi-lamellar vesicles (MLV) in an aqueous medium, wherein the agent contains—in relation to its total weight—
(a11) one or more linear, saturated $C_8$-$C_{30}$ fatty alcohols in a total amount from about 5.0 to about 25.0% by weight, and
(a12) one or more branched, saturated $C_8$-$C_{30}$ fatty alcohols in a total amount from about 1.0 to about 9.0% by weight, and
(a2) at least one ethoxylated fatty alcohol of formula (I),

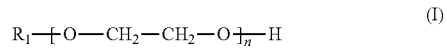

in which
R1 stands for a linear or branched, saturated or unsaturated $C_8$-$C_{30}$ alkyl group and
n stands for an integer from about 10 to about 100
(a3) at least one anionic surfactant of formula (II)

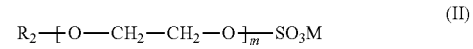

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 0.3 to about 6.0% by weight.

Within the scope of a further embodiment, an agent (A) for changing the colour of keratin fibres, in particular human hair, that has proven to be very particularly preferred is one which comprises unilamellar vesicles (ULV) and/or multi-lamellar vesicles (MLV) in an aqueous medium, wherein the agent contains—in relation to its total weight—
(a11) one or more linear, saturated $C_8$-$C_{30}$ fatty alcohols in a total amount from about 7.0 to about 20.0% by weight, and
(a12) one or more branched, saturated $C_8$-$C_{30}$ fatty alcohols in a total amount from about 1.3 to about 7.0% by weight, and
(a2) at least one ethoxylated fatty alcohol of formula (I),

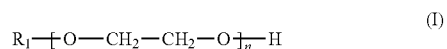

in which
R1 stands for a linear or branched, saturated or unsaturated $C_8$-$C_{30}$ alkyl group and
n stands for an integer from about 10 to about 100
(a3) at least one anionic surfactant of formula (II)

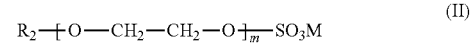

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 0.3 to about 6.0% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 10.0 to about 18.0% by weight, and
(a12) one or more branched, saturated $C_8$-$C_{30}$ fatty alcohols in a total amount from about 1.6 to about 5.0% by weight, and
(a2) at least one ethoxylated fatty alcohol of formula (I), $$R_1 \!-\!\!\left[\!O\!-\!CH_2\!-\!CH_2\!-\!O\right]_{\overline{n}}\!\!-\!H \quad (I)$$

in which
R1 stands for a linear or branched, saturated or unsaturated $C_8$-$C_{30}$ alkyl group and
n stands for an integer from about 10 to about 100
(a3) at least one anionic surfactant of formula (II)

$$R_2 \!-\!\!\left[\!O\!-\!CH_2\!-\!CH_2\!-\!O\right]_{\overline{m}}\!\!-\!SO_3M \quad (II)$$

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 0.3 to about 6.0% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 12.0 to about 16.0% by weight, and
(a12) one or more branched, saturated $C_8$-$C_{30}$ fatty alcohols in a total amount from about 1.9 to about 3.0% by weight, and
(a2) at least one ethoxylated fatty alcohol of formula (I), $$R_1 \!-\!\!\left[\!O\!-\!CH_2\!-\!CH_2\!-\!O\right]_{\overline{n}}\!\!-\!H \quad (I)$$

in which
R1 stands for a linear or branched, saturated or unsaturated $C_8$-$C_{30}$ alkyl group and
n stands for an integer from about 10 to about 100
(a3) at least one anionic surfactant of formula (II)

$$R_2 \!-\!\!\left[\!O\!-\!CH_2\!-\!CH_2\!-\!O\right]_{\overline{m}}\!\!-\!SO_3M \quad (II)$$

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 0.3 to about 6.0% by weight.

Ethoxylated Fatty Alcohols of Formula (I)

Likewise, a significant contribution for the formation of stable uni- and multilamellar vesicles is provided by the ethoxylated fatty alcohols of formula (I). For this reason, the agents as contemplated herein contain, as further essential ingredient (a2), at least one ethoxylated fatty alcohol of formula (I), $$R_1 \!-\!\!\left[\!O\!-\!CH_2\!-\!CH_2\!-\!O\right]_{\overline{n}}\!\!-\!H \quad (I)$$

in which
R1 stands for a linear or branched, saturated or unsaturated $C_8$-$C_{30}$ alkyl group and
n stands for an integer from about 10 to about 100.

The compounds of formula (I) are nonionic compounds. The compounds of formula (I) are ethoxylated $C_8$-$C_{30}$ fatty alcohols with a degree of ethoxylation from about 10 to about 100.

The higher is the degree of ethoxylation, the higher is also the polarity of the corresponding ethoxylated fatty alcohols. In principle, both poorly ethoxylated fatty alcohols (with n up to about 10) and also very highly ethoxylated fatty alcohols (with n up to one hundred) can be used in the agents as contemplated herein.

With regard to the solution to the problem addressed by the present disclosure it has proven to be particularly suitable to use, in this context, compounds of formula (I) in which R1 stands for a linear or branched, saturated or unsaturated $C_8$-$C_{30}$ alkyl group and n stands for an integer from about 10 to about 30.

In a further very particularly preferred embodiment an agent (A) as contemplated herein contains (a2) at least one ethoxylated fatty alcohol of formula (I), in which
R1 stands for a linear or branched, saturated or unsaturated $C_8$-$C_{30}$ alkyl group and
n stands for an integer from about 10 to about 30.

For example, Ceteareth-12 or Ceteareth-20 can be cited as corresponding particularly suitable ethoxylated fatty alcohols with a degree of ethoxylation from about 10 to about 30.

The compound(s) of formula (I) are also preferably used in specific total amounts in the agent (A) as contemplated herein. The agent (A) particularly preferably contains one or more ethoxylated fatty alcohols of formula (I) in a total amount from about 0.5 to about 5.0% by weight, preferably from about 1.0 to about 4.5% by weight, more preferably from about 1.5 to about 4.0% by weight, and particularly preferably from about 2.0 to about 3.5% by weight. In this context as well, all amounts in % by weight relate to the total amount of all ethoxylated fatty alcohols of formula (I) contained in the agent (A), which is set in relation to the total weight of the agent.

In a further very particularly preferred embodiment an agent (A) as contemplated herein contains—in relation to the total weight of the agent (A)—(a2) one or more ethoxylated fatty alcohols of formula (I) in a total amount from about 0.5 to about 5.0% by weight, preferably from about 1.0 to about 4.5% by weight, more preferably from about 1.5 to about 4.0% by weight, and particularly preferably from about 2.0 to about 3.5% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 5.0 to about 25.0% by weight, and
(a12) one or more branched, saturated $C_8$-$C_{30}$ fatty alcohols in a total amount from about 1.0 to about 9.0% by weight, and
(a2) one or more ethoxylated fatty alcohols of formula (I) in a total amount from about 0.5 to about 5.0% by weight,

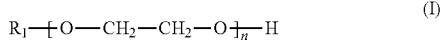

(I)

in which
R1 stands for a linear or branched, saturated or unsaturated $C_8$-$C_{30}$ alkyl group and
n stands for an integer from about 10 to about 100
(a3) at least one anionic surfactant of formula (II)

(II)

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$), and
(a4) stands for one or more colour-changing salts from the group of sulfates, hydrogen sulfates, chlorides and/or bromides in a total amount of from about 0.3 to about 6.0% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 7.0 to about 20.0% by weight, and
(a12) one or more branched, saturated $C_8$-$C_{30}$ fatty alcohols in a total amount from about 1.3 to about 7.0% by weight, and
(a2) one or more ethoxylated fatty alcohols of formula (I) in a total amount from about 1.0 to about 4.5% by weight,

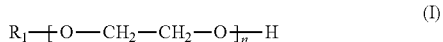

(I)

in which
R1 stands for a linear or branched, saturated or unsaturated $C_8$-$C_{30}$ alkyl group and
n stands for an integer from about 10 to about 100
(a3) at least one anionic surfactant of formula (II)

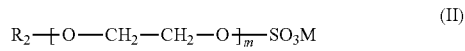

(II)

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$), and
(a4) stands for one or more colour-changing salts from the group of sulfates, hydrogen sulfates, chlorides and/or bromides in a total amount of from about 0.3 to about 6.0% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 10.0 to about 18.0% by weight, and
(a12) one or more branched, saturated $C_8$-$C_{30}$ fatty alcohols in a total amount from about 1.6 to about 5.0% by weight, and
(a2) one or more ethoxylated fatty alcohols of formula (I) in a total amount from about 1.5 to about 4.0% by weight,

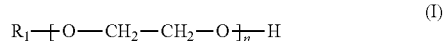

(I)

in which
R1 stands for a linear or branched, saturated or unsaturated $C_8$-$C_{30}$ alkyl group and
n stands for an integer from about 10 to about 100, and
(a3) at least one anionic surfactant of formula (II)

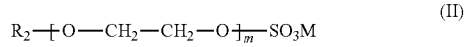

(II)

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 0.3 to about 6.0% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 12.0 to about 16.0% by weight, and
(a12) one or more branched, saturated $C_8$-$C_{30}$ fatty alcohols in a total amount from about 1.9 to about 3.0% by weight, and (a2) one or more ethoxylated fatty alcohols of formula (I) in a total amount from about 2.0 to about 3.5% by weight,

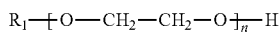
(I)

in which
R1 stands for a linear or branched, saturated or unsaturated $C_8$-$C_{30}$ alkyl group and
n stands for an integer from about 10 to about 100
(a3) at least one anionic surfactant of formula (II)

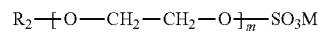
(II)

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 0.3 to about 6.0% by weight.

Anionic Surfactants of Formula (II)

A rather particular contribution for the formation of stable uni- and multilamellar vesicles is provided by the anionic surfactants of formula (II). For this reason, the agents as contemplated herein contain, as further essential ingredient (a3), at least one anionic surfactant of formula (II),

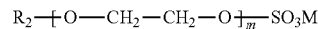
(II)

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$).

The anionic surfactants of formula (II) may be fatty alcohol sulfates (in the case of m=0), wherein R2 represents the fatty alcohol group (i.e. a $C_8$-$C_{30}$ alkyl group) of the surfactant.

Furthermore, the anionic surfactants of formula (II) may also be ethoxylated fatty alcohol sulfates, wherein the number m represents the degree of ethoxylation and can stand for an integer from about 1 to about 10.

The grouping M represents the counterion for neutralisation of the sulfate group and can stand for a hydrogen atom; in this case the compound of formula (II) is present in the form of its acid. The protonated form is in equilibrium with its anion in the aqueous carrier medium of the agent. The grouping M may furthermore also stand for a sodium ion ($Na^+$), a potassium ion ($K^+$) or for an ammonium ion ($NH4^+$).

In order to produce particularly stable formulations with unilamellar and multilamellar vesicles, it has proven to be particularly advantageous if the agents as contemplated herein contains both a non-ethoxylated fatty alcohol sulfate (i.e. a compound of formula (II), in which m stands for the number 0) and an ethoxylated fatty alcohol sulfate (i.e. a compound of formula (II), in which m stands for the number from about 1 to about 10, particularly preferably for the number from about 1 to about 5).

In a further very particularly preferred embodiment an agent (A) as contemplated herein comprises
(a31) at least one first anionic surfactant of formula (II), in which
R2 stands for a linear, saturated $C_8$-$C_{30}$ alkyl group and m stands for the number 0, and
(a32) at least one second anionic surfactant of formula (II), in which
R2 stands for a linear, saturated $C_8$-$C_{30}$ alkyl group and m stands for an integer from 1 to 5.

A person skilled in the art knows the anionic surfactants of formula (II) under the general term fatty alcohol sulfates (for example sodium lauryl sulfate, sodium cetyl sulfate, sodium stearyl sulfate, sodium cetearyl sulfate) or fatty alcohol ether sulfate (for example sodium laureth sulfate, etc.). These anionic surfactants, in the sense of the present disclosure, do not fall explicitly under the group of colour-changing sulfate salts, since in the case of the anionic surfactants the sulfate is part of the organic group, but as contemplated herein colour-changing salts are understood to mean only cationic compounds with sulfate anion (i.e. $SO_4^{2-}$). In addition, the anionic surfactants (a3) do not have any colour-changing effects on keratin fibres.

The compound(s) of formula (II) are also preferably used in specific total amounts in the agent (A) as contemplated herein. The agent (A) particularly preferably contains one or more anionic surfactants of formula (II) in a total amount from about 0.5 to about 4.8% by weight, preferably from about 0.5 to about 4.2% by weight, more preferably from about 0.5 to about 3.8% by weight, and particularly preferably from about 1.0 to about 3.0% by weight. In this context as well, all amounts in % by weight relate to the total amount of all anionic surfactants of formula (II) contained in the agent (A), which is set in relation to the total weight of the agent.

In a further very particularly preferred embodiment an agent (A) as contemplated herein contains—in relation to the total weight of the agent (A)—(a3) one or more anionic surfactants of formula (II) in a total amount from about 0.5 to about 4.8% by weight, preferably from about 0.5 to about 4.2% by weight, more preferably from about 0.5 to about 3.8% by weight, and particularly preferably from about 1.0 to about 3.0% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 5.0 to about 25.0% by weight, and
(a12) one or more branched, saturated $C_8$-$C_{30}$ fatty alcohols in a total amount from about 1.0 to about 9.0% by weight, and
(a2) one or more ethoxylated fatty alcohols of formula (I) in a total amount from about 0.5 to about 5.0% by weight,

(I)

in which
R1 stands for a linear or branched, saturated or unsaturated $C_8$-$C_{30}$ alkyl group and
n stands for an integer from about 10 to about 100
(a3) one or more anionic surfactants of formula (II) in a total amount from about 0.5 to about 4.8% by weight,

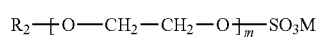

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$), and
(a4) stands for one or more colour-changing salts from the group of sulfates, hydrogen sulfates, chlorides and/or bromides in a total amount of from about 0.3 to about 6.0% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 7.0 to about 20.0% by weight, and
(a12) one or more branched, saturated $C_8$-$C_{30}$ fatty alcohols in a total amount from about 1.3 to about 7.0% by weight, and
(a2) one or more ethoxylated fatty alcohols of formula (I) in a total amount from about 1.0 to about 4.5% by weight,

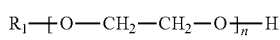

in which
R1 stands for a linear or branched, saturated or unsaturated $C_8$-$C_{30}$ alkyl group and
n stands for an integer from about 10 to about 100
(a3) one or more anionic surfactants of formula (II) in a total amount from about 0.5 to about 4.2% by weight,

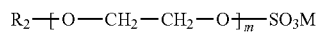

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$), and
(a4) stands for one or more colour-changing salts from the group of sulfates, hydrogen sulfates, chlorides and/or bromides in a total amount of from about 0.3 to about 6.0% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 10.0 to about 18.0% by weight, and
(a12) one or more branched, saturated $C_8$-$C_{30}$ fatty alcohols in a total amount from about 1.6 to about 5.0% by weight, and
(a2) one or more ethoxylated fatty alcohols of formula (I) in a total amount from about 1.5 to about 4.0% by weight,

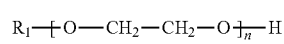

in which
R1 stands for a linear or branched, saturated or unsaturated $C_8$-$C_{30}$ alkyl group and
n stands for an integer from about 10 to about 100, and
(a3) one or more anionic surfactants of formula (II) in a total amount from about 0.5 to about 3.8% by weight,

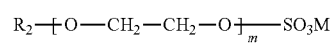

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 0.3 to about 6.0% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 12.0 to about 16.0% by weight, and
(a12) one or more branched, saturated $C_8$-$C_{30}$ fatty alcohols in a total amount from about 1.9 to about 3.0% by weight, and
(a2) one or more ethoxylated fatty alcohols of formula (I) in a total amount from about 2.0 to about 3.5% by weight,

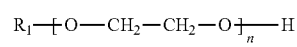

in which
R1 stands for a linear or branched, saturated or unsaturated $C_8$-$C_{30}$ alkyl group and
n stands for an integer from about 10 to about 100
(a3) one or more anionic surfactants of formula (II) in a total amount from about 1.0 to about 3.0% by weight,

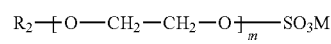

in which

R2 stands for a linear or branched, saturated or unsaturated $C_8$-$C_{30}$ alkyl group, m stands for an integer from 0 to about 10, and M stands for a hydrogen atom, an equivalent of a sodium ion, a potassium ion, or an ammonium ion ($NH_4^+$), (a4) stands for one or more colour-changing salts from the group of sulfates, hydrogen sulfates, chlorides and/or bromides in a total amount of from about 0.3 to about 6.0% by weight.

Colour-Changing Salts from the Group of Sulfates, Hydrogen Sulfates, Chlorides and/or Bromides (a4)

The agents as contemplated herein are employed for changing the colour of keratin fibres, and therefore the agents contain at least one colour-changing compound. Substantive dyes and in particular oxidation dye precursors fall within the group of colour-changing compounds as contemplated herein.

Oxidation dye precursors can be divided into developers and couplers, wherein the developers, due to their greater sensitivity to oxygen, are usually used in the form of their physiologically acceptable colour-changing salts (for example in the form of their sulfates, hydrogen sulfates, chlorides or bromides).

Within the scope of oxidative dyeing, coupler components alone do not result in significant dyeing, and instead always require the presence of developer components. Since couplers are not as sensitive to oxygen as developers, they likewise can be used in the form of their colour-changing salts in the preparations but are often also used in free form (i.e. not in salt form).

During the course of the works leading to this present disclosure it was found that in particular shades having a high content of oxidation dye precursors, i.e. brown shades, black shades or other dark shades, in the can be very well stabilised by the agents as contemplated herein This effect is particularly pronounced when oxidation dyes are used in the form of their physiologically acceptable salts.

Preferred physiologically acceptable colour-changing salts of developers are, for example, phenylenediamine sulfate, phenylenediamine monohydrochloride, phenylenediamine dihydrochloride, p-toluene diamine sulfate, p-toluene diamine monohydrochloride, p-toluene diamine dihydrochloride, 2-(2-hydroxyethyl)-p-phenylenediamine sulfate, 2-(2-hydroxyethyl)-p-phenylenediamine monohydrochloride, 2-(2-hydroxyethyl)-p-phenylenediamine dihydrochloride, N,N-bis-(2-hydroxyethyl)-p-phenylenediamine sulfate, N,N-bis-(2-hydroxyethyl)-p-phenylenediamine monohydrochloride, N,N-bis-(2-hydroxyethyl)-p-phenylenediamine dihydrochloride, 2-methoxymethyl-p-phenylenediamine sulfate, 2-methoxymethyl-p-phenylenediamine monohydrochloride, 2-methoxymethyl-p-phenylenediamine dihydrochloride, p-aminophenol hydrogen sulfate, p-aminophenol monohydrochloride, 4-amino-3-methylphenol hydrogen sulfate, 4-amino-3-methylphenol chloride, 2,4,5,6-tetraaminopyrimidine monosulfate, 2,4,5,6-tetraaminopyrimidine disulfate, 2,4,5,6-tetraaminopyrimidine monohydrochloride, 2,4,5,6-tetraaminopyrimidine dihydrochloride, 2,4,5,6-tetraaminopyrimidine trihydrochloride, 2,4,5,6-tetraaminopyrimidine tetrahydrochloride, 4-hydroxy-2,5,6-triaminopyrimidine sulfate, 4-hydroxy-2,5,6-triaminopyrimidine monohydrochloride, 4-hydroxy-2,5,6-triaminopyrimidine dihydrochloride, 4-hydroxy-2,5,6-triaminopyrimidine trihydrochloride, 4,5-diamino-1-(2-hydroxyethyl)-1H-pyrazole sulfate, 4,5-diamino-1-(2-hydroxyethyl)-1H-pyrazole monohydrochloride and/or 4,5-diamino-1-(2-hydroxyethyl)-1H-pyrazole dihydrochloride.

In a further very particularly preferred embodiment an agent (A) as contemplated herein contains (a4) one or more colour-changing salts from the group of phenylenediamine sulfate, phenylenediamine monohydrochloride, phenylenediamine dihydrochloride, p-toluene diamine sulfate, p-toluene diamine monohydrochloride, p-toluene diamine dihydrochloride, 2-(2-hydroxyethyl)-p-phenylenediamine sulfate, 2-(2-hydroxyethyl)-p-phenylenediamine monohydrochloride, 2-(2-hydroxyethyl)-p-phenylenediamine dihydrochloride, N,N-bis-(2-hydroxyethyl)-p-phenylenediamine sulfate, N,N-bis-(2-hydroxyethyl)-p-phenylenediamine monohydrochloride, N,N-bis-(2-hydroxyethyl)-p-phenylenediamine dihydrochloride, 2-methoxy methyl-p-phenylenediamine sulfate, 2-methoxymethyl-p-phenylenediamine monohydrochloride, 2-methoxymethyl-p-phenylenediamine dihydrochloride, p-aminophenol hydrogen sulfate, p-aminophenol monohydrochloride, 4-amino-3-methylphenol hydrogen sulfate, 4-amino-3-methylphenol chloride, 2,4,5,6-tetraaminopyrimidine monosulfate, 2,4,5,6-tetraaminopyrimidine disulfate, 2,4,5,6-tetraaminopyrimidine monohydrochloride, 2,4,5,6-tetraaminopyrimidine dihydrochloride, 2,4,5,6-tetraaminopyrimidine trihydrochloride, 2,4,5,6-tetraaminopyrimidine tetrahydrochloride, 4-hydroxy-2,5,6-triaminopyrimidine sulfate, 4-hydroxy-2,5,6-triaminopyrimidine monohydrochloride, 4-hydroxy-2,5,6-triaminopyrimidine dihydrochloride, 4-hydroxy-2,5,6-triaminopyrimidine trihydrochloride, 4,5-diamino-1-(2-hydroxyethyl)-1H-pyrazole sulfate, 4,5-diamino-1-(2-hydroxyethyl)-1H-pyrazole monohydrochloride and/or 4,5-diamino-1-(2-hydroxyethyl)-1H-pyrazole dihydrochloride.

Oxidation dye precursors of the developer type are usually derivatives of p-phenylenediamine, p-aminophenol, or heterocyclic compounds with at least one, preferably at least two amino groups. For conversion into their salts, the amino groups contained in these structures are protonated and have the corresponding equivalent of sulfate anions, hydrogen sulfate anions, chloride anions and/or bromide anions for neutralisation of this positive charge.

In the case of p-toluene diamine sulfate, this is for example the compound toluene diamine×$H_2SO_4$. Both amino groups are present in protonated form (in the form of ammonium ions) and the two cationic charges now contained in the molecule are neutralised by a sulfate anion ($SO_4^{2-}$). In the case of p-toluene diamine monohydrochloride, this is therefore the compound toluene diamine×HCl. One of the two amino groups is present in protonated form and has a chloride as counterion. In the case of p-toluene diamine dihydrochloride, this is the compound toluene diamine×2 HCl. Both amino groups are present in protonated form and have two chlorides as counterion. The salts of the further oxidation dyes of the developer type are composed similarly.

Depending on the desired colour result, oxidation precursors of the developer and coupler type are used in different amounts in the dye agent.

If dyeing in a blonde shade is desired, the use of oxidation precursors in a total amount below about 0.3% by weight is thus usually sufficient.

If, however, the user wishes to achieve dyeing in a very dark shade, for example in a dark brown shade or in a black shade, this necessitates the use of oxidation dye precursors in a total amount of at least about 2.0% by weight, often about 3.0% by weight, and in the case of particularly dark shades (black) even above about 4.5% by weight (in relation to the total weight of the dye agent (A)).

The higher is the colourant content, the more difficult it is to stabilise the agent. In this regard it has been found that in particular the stabilisation of brown or black shades is very easily possible by the formation of uni- and multilamellar vesicles. The agents (A) as contemplated herein therefore preferably contain one or more colour-changing salts (a4) from the group of sulfates, hydrogen sulfates, chlorides and/or bromides in a total amount from about 0.5 to about 5.5% by weight, preferably from about 0.7 to about 5.0% by weight, more preferably from about 0.9 to about 4.5% by weight, and very particularly preferably from about 2.1 to about 3.4% by weight. In this context as well, all amounts in % by weight relate to the total amount of all colour-changing salts (a4) in the agent, which is set in relation to the total weight of the agent.

In a further very particularly preferred embodiment an agent (A) as contemplated herein contains—in relation to the total weight of the agent (A)—(a4) one or more colour-changing salts from the group of sulfates, hydrogen sulfates, chlorides and/or bromides in a total amount from about 0.5 to about 5.5% by weight, preferably from about 0.7 to about 5.0% by weight, more preferably from about 0.9 to about 4.5% by weight, and very particularly preferably from about 2.1 to about 3.4% by weight.

Within the scope of a further embodiment, an agent (A) for changing the colour of keratin fibres, in particular human hair, that has proven to be very particularly preferred is one which comprises unilamellar vesicles (ULV) and/or multi-lamellar vesicles (MLV) in an aqueous medium, wherein the agent contains—in relation to its total weight—
(a11) one or more linear, saturated $C_8$-$C_{30}$ fatty alcohols in a total amount from about 5.0 to about 25.0% by weight, and
(a12) one or more branched, saturated $C_8$-$C_{30}$ fatty alcohols in a total amount from about 1.0 to about 9.0% by weight, and
(a2) one or more ethoxylated fatty alcohols of formula (I) in a total amount from about 0.5 to about 5.0% by weight,

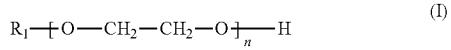
(I)

in which
R1 stands for a linear or branched, saturated or unsaturated $C_8$-$C_{30}$ alkyl group and
n stands for an integer from about 10 to about 100
(a3) one or more anionic surfactants of formula (II) in a total amount from about 0.5 to about 4.8% by weight,

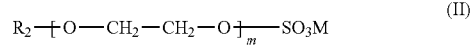
(II)

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$), and
(a4) stands for one or more colour-changing salts from the group of sulfates, hydrogen sulfates, chlorides and/or bromides in a total amount of from about 0.5 to about 5.5% by weight.

Within the scope of a further embodiment, an agent (A) for changing the colour of keratin fibres, in particular human hair, that has proven to be very particularly preferred is one which comprises unilamellar vesicles (ULV) and/or multi-lamellar vesicles (MLV) in an aqueous medium, wherein the agent contains—in relation to its total weight—
(a11) one or more linear, saturated $C_8$-$C_{30}$ fatty alcohols in a total amount from about 7.0 to about 20.0% by weight, and
(a12) one or more branched, saturated $C_8$-$C_{30}$ fatty alcohols in a total amount from about 1.3 to about 7.0% by weight, and
(a2) one or more ethoxylated fatty alcohols of formula (I) in a total amount from about 1.0 to about 4.5% by weight,

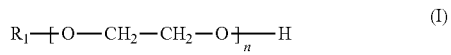
(I)

in which
R1 stands for a linear or branched, saturated or unsaturated $C_8$-$C_{30}$ alkyl group and
n stands for an integer from about 10 to about 100
(a3) one or more anionic surfactants of formula (II) in a total amount from about 0.5 to about 4.2% by weight,

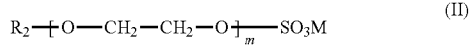
(II)

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$), and
(a4) stands for one or more colour-changing salts from the group of sulfates, hydrogen sulfates, chlorides and/or bromides in a total amount of from about 0.7 to about 5.0% by weight.

Within the scope of a further embodiment, an agent (A) for changing the colour of keratin fibres, in particular human hair, that has proven to be very particularly preferred is one which comprises unilamellar vesicles (ULV) and/or multi-lamellar vesicles (MLV) in an aqueous medium, wherein the agent contains—in relation to its total weight—
(a11) one or more linear, saturated $C_8$-$C_{30}$ fatty alcohols in a total amount from about 10.0 to about 18.0% by weight, and
(a12) one or more branched, saturated $C_8$-$C_{30}$ fatty alcohols in a total amount from about 1.6 to about 5.0% by weight, and
(a2) one or more ethoxylated fatty alcohols of formula (I) in a total amount from about 1.5 to about 4.0% by weight,

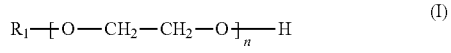
(I)

in which
R1 stands for a linear or branched, saturated or unsaturated $C_8$-$C_{30}$ alkyl group and
n stands for an integer from about 10 to about 100, and
(a3) one or more anionic surfactants of formula (II) in a total amount from about 0.5 to about 3.8% by weight,

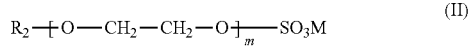

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 0.9 to about 4.5% by weight.

Within the scope of a further embodiment, an agent (A) for changing the colour of keratin fibres, in particular human hair, that has proven to be very particularly preferred is one which comprises unilamellar vesicles (ULV) and/or multilamellar vesicles (MLV) in an aqueous medium, wherein the agent contains—in relation to its total weight—
(a11) one or more linear, saturated $C_8$-$C_{30}$ fatty alcohols in a total amount from about 12.0 to about 16.0% by weight, and
(a12) one or more branched, saturated $C_8$-$C_{30}$ fatty alcohols in a total amount from about 1.9 to about 3.0% by weight, and
(a2) one or more ethoxylated fatty alcohols of formula (I) in a total amount from about 2.0 to about 3.5% by weight,

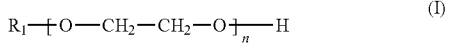

in which
R1 stands for a linear or branched, saturated or unsaturated $C_8$-$C_{30}$ alkyl group and
n stands for an integer from about 10 to about 100
(a3) one or more anionic surfactants of formula (II) in a total amount from about 1.0 to about 3.0% by weight,

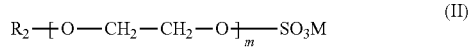

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 2.1 to about 3.4% by weight.

Within the scope of a further embodiment, an agent (A) for changing the colour of keratin fibres, in particular human hair, that has proven to be very particularly preferred is one which comprises multilamellar vesicles (MLV) in an aqueous medium, wherein the agent contains—in relation to its total weight—
(a11) one or more linear, saturated $C_8$-$C_{30}$ fatty alcohols in a total amount from about 12.0 to about 16.0% by weight, and
(a12) one or more branched, saturated $C_8$-$C_{30}$ fatty alcohols in a total amount from about 1.9 to about 3.0% by weight, and
(a2) one or more ethoxylated fatty alcohols of formula (I) in a total amount from about 2.0 to about 3.5% by weight,

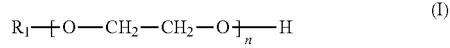

in which
R1 stands for a linear or branched, saturated or unsaturated $C_8$-$C_{30}$ alkyl group and
n stands for an integer from about 10 to about 100
(a3) one or more anionic surfactants of formula (II) in a total amount from about 1.0 to about 3.0% by weight,

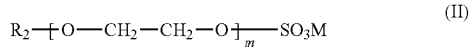

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$),
(a4) stands for one or more colour-changing salts from the group of sulfates, hydrogen sulfates, chlorides and/or bromides in a total amount of from about 2.1 to about 3.4% by weight.

Oxidation dye precursors of the developer type can be contained as the sole colour-changing compounds in the agent as contemplated herein. It is preferred, however, as contemplated herein if the dye agent (A) additionally contains at least one oxidation dye precursor of the coupler type (referred to as a coupler for short).

Within the scope of oxidative dyeing, coupler components alone do not result in significant dyeing, and instead always require the presence of developer components. Coupler components as contemplated herein allow at least one substitution of a chemical groups of the coupler by the oxidised form of the developer component. Here, covalent bonds form between the coupler and developer component.

At least one compound from one of the following classes is preferably selected as coupler component suitable as contemplated herein:
m-aminophenol and/or derivatives thereof,
m-diaminobenzene and/or derivatives thereof,
o-diaminobenzene and/or derivatives thereof,
o-aminophenol derivatives, such as o-aminophenol,
naphthalene derivatives with at least one hydroxy group,
di- or trihydroxybenzene and/or derivatives thereof,
pyridine derivatives,
pyrimidine derivatives,
monohydroxyindol derivatives and/or monoaminoindol derivatives,
monohydroxyindoline derivatives and/or monoaminoindoline derivatives,
pyrazolone derivative, such as 1-phenyl-3-methylpyrazol-5-one,
morpholine derivatives, such as 6-hydroxybenzomorpholine or 6-aminobenzomorpholine,
quinoxaline derivatives, such as 6-methyl-1,2,3,4-tetrahydroquinoxaline.

Mixtures of two or more compounds from one or more of these classes also correspond to the present disclosure within the scope of this embodiment.

In a further embodiment an agent as contemplated herein contains at least one oxidation dye precursor of the coupler type, which is selected from the group of 3-aminophenol, 5-amino-2-methylphenol, 3-amino-2-chloro-6-methylphenol, 2-hydroxy-4-aminophenoxy ethanol, 5-amino-4-chloro-2-methylphenol, 5-(2-hydroxyethyl)-amino-2-methylphenol, 2,4-dichloro-3-aminophenol, 2-aminophenol, 3-phenylenediamine, diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol, 2-[3-morpholin-4-ylphenyl)amino]ethanol, 3-amino-4-(2-methoxy¬ethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline and 7-hydroxyindoline, and the physiologically acceptable colour-changing salts thereof.

In addition to the oxidation dye precursors or instead of these, the dye agents (F) as contemplated herein can contain at least one substantive dye (D). These are colourants that are taken up directly on the hair and do not require an oxidative process in order to form the colour. Substantive dyes are usually nitrophenylenediamines, nitroaminophenols, azo dyes, anthraquinones, triarylmethane dyes or indophenols.

Substantive dyes can be divided into anionic, cationic and nonionic substantive dyes.

Cationic dyes which are present in the form of their sulfates, hydrogen sulfates, chlorides and/or bromides likewise fall under the definition of the colouring salts (a4) in the sense of the present disclosure.

In particular, nonionic nitro and quinone dyes and neutral azo dyes are suitable as nonionic substantive dyes. Preferred nonionic substantive dyes are the compounds known under the following international names or trade names: HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and colour-changing salts thereof, 2-amino-6-chloro-4-nitrophenol, 4-ethylamino-3-nitrobenzoic acid and 2-chloro-6-ethylamino-4-nitrophenol.

Anionic substantive dyes carry at least one negative charge and are also referred to in the literature as acid dyes. Preferred anionic substantive dyes are the compounds known under the international names or trade names: bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Cationic dyes are exemplified by the presence of at least one positive charge. In the English literature, cationic dyes are also referred to as "basic dyes". Preferred cationic substantive dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31 and Basic Red 51.

As already described beforehand, the stabilisation of emulsions is often more difficult, the higher is the salt content of an emulsion. Emulsions in which high amounts of cationic substantive dyes are used, usually are also more difficult to stabilise than emulsions having a low dye content or emulsions that contain only nonionic substantive dyes.

During the course of the works performed, it was found that the dye agents (A) present in emulsion form in particular can be stabilised very well also if the dye agent (A) contains, as colouring salts (a4), substantive cationic dyes which are present in the form of their sulfates, hydrogen sulfates, chlorides and/or bromides.

In principle, the substantive dyes can be contained in a total amount from about 0.001 to about 10% by weight in the dye agent (A) as contemplated herein.

If, however, cationic dyes in the form of their sulfate salts, hydrogen sulfate salts, chloride salts and/or bromide salts are used as substantive dyes, they fall in the group of colouring salts (a4) and are used in the previously described minimum and maximum amounts preferred and particularly preferred as contemplated herein.

Phosphorous Compounds

It is known from the prior art that unilamellar and multilamellar vesicles form easily with use of typical vesicle formers. Typical vesicle formers are, above all, the phospholipids or phosphoaminolipids known from biological processes. These phosphorous vesicle formers are generally expensive, and therefore more effective and more economical methods are constantly being sought in order to be able to form unilamellar and multilamellar vesicles also without use of these phosphorous compounds.

It has surprisingly been found that it is possible to form uni- and multilamellar vesicles in the agent (A) as contemplated herein also without use of the typical phosphorous compounds by use of the previously described essential ingredients (a1), (a2), (a3) and (a4).

For this reason, it is very particularly preferred if the agent (A) contains—in relation to the total weight of the agent (A)—phosphorous compounds in a total amount of less than about 0.1% by weight, preferably of less than about 0.05% by weight.

In a further very particularly preferred embodiment an agent (A) as contemplated herein contains—in relation to the total weight of the agent (A)—phosphorous compounds in a total amount of less than about 0.1% by weight, preferably of less than about 0.05% by weight.

In the sense of the present disclosure, phosphorous compounds are understood to mean all inorganic and organic compounds, which may be uncharged or charged, the structures of which comprise at least one phosphorus atom (either in the organic part and/or in the inorganic part) as structural component.

$C_8$-$C_{30}$ Fatty Acid Monoglycerides, $C_8$-$C_{30}$ Fatty Acid Diglycerides $C_8$-$C_{30}$ Fatty Acid Triglycerides (a5)

It has proven to be particularly advantageous, for the formation of the unilamellar and multilamellar vesicles, if the agents as contemplated herein also contain additionally at least one $C_8$-$C_{30}$ fatty acid monoglyceride, one $C_8$-$C_{30}$ fatty acid diglyceride and/or one $C_8$-$C_{30}$ fatty acid triglyceride as further particularly preferred ingredient (a5).

In a further very particularly preferred embodiment an agent (A) as contemplated herein contains (a5) at least one $C_8$-$C_{30}$ fatty acid monoglyceride, one $C_8$-$C_{30}$ fatty acid diglyceride and/or one $C_8$-$C_{30}$ fatty acid triglyceride A $C_8$-$C_{30}$ fatty acid triglyceride is understood in the sense of the present disclosure to mean the triester of the trivalent alcohol glycerol with three equivalent fatty acids. Both structurally identical and different fatty acids within a triglyceride molecule can be involved in the ester formations.

Fatty acids, as contemplated herein, are understood to mean saturated or unsaturated, unbranched or branched, unsubstituted or substituted $C_8$-$C_{30}$ carboxylic acids. Unsaturated fatty acids can be mono- or polyunsaturated. In the case of an unsaturated fatty acid the C—C double bond(s) thereof can have the cis or trans configuration.

The fatty acid triglycerides that are particularly suitable are those in which at least one of the ester groups starting from glycerol is formed with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

The fatty acid triglycerides can also be of natural origin. The fatty acid triglycerides occurring in soybean oil, peanut oil, olive oil, sunflower oil, macadamia nut oil, moringa oil, apricot kernel oil, marula oil and/or possibly hardened castor oil and mixtures thereof are particularly suitable for use in the product as contemplated herein.

A $C_8$-$C_{30}$ fatty acid monoglyceride is understood to mean the monoester of the trivalent alcohol glycerol with an equivalent fatty acid. Here, either the middle hydroxy group of the glycerol or the terminal hydroxy group of the glycerol can be esterified with the fatty acid.

The $C_8$-$C_{30}$ fatty acid monoglycerides that are particularly suitable are those in which a hydroxy group of the glycerol is esterified with a fatty acid, wherein the fatty acids are selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenoic acid] or nervonic acid [(15Z)-tetracos-15-enoic acid].

A $C_8$-$C_{30}$ fatty acid diglyceride is understood to mean the diester of the trivalent alcohol glycerol with two equivalent fatty acids. Here, either the middle and a terminal hydroxy group of glycerol can be esterified with two equivalents fatty acid, or both terminal hydroxy groups of glycerol are esterified with one fatty acid each. The glycerol can be esterified here both with two structurally identical fatty acids and with two different fatty acids.

The fatty acid diglycerides that are particularly suitable are those in which at least one of the ester groups starting from glycerol is formed with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

Within the group of $C_8$-$C_{30}$ fatty acid monoglycerides, $C_8$-$C_{30}$ fatty acid diglycerides and/or $C_8$-$C_{30}$ fatty acid triglycerides, the $C_8$-$C_{30}$ fatty acid monoglycerides have the best properties. Thus, at least one $C_8$-$C_{30}$ fatty acid monoglyceride is very particularly preferably used in the agent (a) as contemplated herein.

The compound(s) from group (a5) are also preferably used in specific total amounts in the agent (A) as contemplated herein. The agent (A) particularly preferably contains one or more $C_8$-$C_{30}$ fatty acid monoglycerides, a $C_8$-$C_{30}$ fatty acid diglyceride and/or a $C_8$-$C_{30}$ fatty acid triglyceride in a total amount from about 1.0 to about 6.0% by weight, preferably from about 1.5 to about 5.5% by weight, more preferably from about 2.0 to about 5.0% by weight, and very particularly preferably from about 2.5 to about 4.5% by weight. In this regard as well, all values in % by weight relate to the total amount of all compounds from the group (a5) contained in the agent (A), which is set in relation to the total weight of the agent.

The agent (A) very particularly preferably contains one or more $C_8$-$C_{30}$ fatty acid monoglycerides in a total amount from about 1.0 to about 6.0% by weight, preferably from about 1.5 to about 5.5% by weight, more preferably from about 2.0 to about 5.0% by weight, and very particularly preferably from about 2.5 to about 4.5% by weight.

In a further very particularly preferred embodiment an agent (A) as contemplated herein contains—in relation to the total weight of the agent (A)—(a5) one or more $C_8$-$C_{30}$ fatty acid monoglycerides in a total amount from about 1.0 to about 6.0% by weight, preferably from about 1.5 to about 5.5% by weight, more preferably from about 2.0 to about 5.0% by weight, and very particularly preferably from about 2.5 to about 4.5% by weight.

Water Phase

The agents as contemplated herein comprise an aqueous medium which likewise contributes to the formation of the vesicles or forms the hydrophilic inner space and/or outer space in which the uni- and multilamellar vesicles are disposed. The agent (A) as contemplated herein preferably contains—in relation to its total weight—water in an amount from about 60.0 to about 85.0% by weight, preferably from about 65.0 to about 75.0% by weight, more preferably from about 60.0 to about 80.0% by weight, and particularly preferably from about 65 to about 75.0% by weight.

In a further very particularly preferred embodiment an agent (A) as contemplated herein contains—in relation to the total weight of the agent (A)—water in an amount from about 60.0 to about 85.0% by weight, preferably from about 65.0 to about 75.0% by weight, more preferably from about 60.0 to about 80.0% by weight, and very particularly preferably from about 65 to about 75.0% by weight.

Multi-Component Packaging Unit (Kit-of-Parts)

The agents as contemplated herein are agents for changing the colour of keratin fibres. In particular, they are agents for the dyeing, especially oxidative dyeing, of human hair.

In order to avoid incompatibilities and in order to prevent a premature, undesirable colourant formation, the colouring cream and the oxidant preparation necessary for the oxidative colouring are always packaged separately from one another and are brought into contact with one another just before use. For the consumer, the two components are provided preferably in the form of a multi-component packaging unit (kit-of-parts).

A second subject of the present disclosure is therefore a multi-component packaging unit (kit-of-parts) for the oxidative dyeing of keratin fibres, in particular human hair, comprising, packaged separately from one another,
a container (I) containing a cosmetic agent (A) and
a container (II) containing a cosmetic agent (B), wherein
the agent (A) in container (I) is an agent as has been disclosed in detail in the description of the first subject of the present disclosure, and
the agent (B) in the container (II) is an oxidant preparation (B) containing hydrogen peroxide.

Oxidant Preparation (B)

The oxidant preparation (B) contains hydrogen peroxide as oxidant. The hydrogen peroxide can be provided either as hydrogen peroxide itself or also in the form of its solid addition products with organic or inorganic compounds, such as urea, melamine and sodium borate.

The amount of oxidant in the oxidant preparation (B)—in relation to the total weight of the oxidant preparation (B)—is preferably from about 0.5 to about 12% by weight, preferably from about 2 to about 10% by weight, particularly preferably from about 3 to about 6% by weight (calculated as 100% $H_2O_2$).

Such oxidant preparations are preferably aqueous, flowable oxidant preparations. Here, preferred preparations are exemplified in that the flowable oxidant preparation—in relation to its weight—contains from about 40 to about 90% by weight, preferably from about 50 to about 85% by weight, particularly preferably from about 55 to about 85% by weight, more preferably from about 60 to about 85% by weight, and in particular from about 70 to about 85% by weight of water.

It has also proven to be advantageous if the oxidant preparation (B) contains at least one stabiliser or complexing agent. Conventional complexing agents and stabilisers that are preferred within the scope of the present disclosure are, for example polyoxycarboxylic acids, polyamines, ethylenediaminetetraacetic acid (EDTA), N-hydroxyethylethylenediaminetriacetic acid, diethylenetriaminepentaacetic acid (DTPA), ethylenediaminedisuccinic acid (EDDS), hydroxyethyliminodiacetic acid, nitridodiacetic acid-3-propionic acid, isoserindiacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediaminediglutaric acid (EDGA), 2-hydroxypropylendiamindisuccinc acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), diaminoalkyldi-(sulfosuccinic acid) (DDS), ethylenedicysteic acid (EDC), ethylenediamine-N—N'-bis(ortho-hydroxy phenyl)acetic acid (EDDHA), N-2-hydroxyethylamine-N,N-diacetic acid, glyceryliminodiacetic acid, iminodiacetic acid-N-2-hydroxypropylsulfonic acid, aspartic acid-N-carboxymethyl-N-2,5-hydroxypropyl-3-sulfonic acid, β-alanine-N,N-diacetic acid, aspartic acid-N,N'-diacetic acid, aspartic acid-N-monoacetic acid, dipicolinic acid, and colour-changing salts and/or derivatives thereof, geminal diphosphonic acids such as 1-hydroxyethane-1,1-diphosphonic acid (HEDP), higher homologues thereof with up to 8 carbon atoms and hydroxy or amino group-containing derivatives hereof and 1-aminoethane-1,1-diphosphonic acid higher homologues thereof with up to 8 carbon atoms and hydroxy or amino group-containing derivatives, aminophosphonic acids such as ethylenediaminetetra(methylenephosphonic acid) (EDTMP), diethylene-triaminepenta(methylenephosphonic acid) (DTPMP) and higher homologues thereof, or nitrilotri(methylenephosphonic acid), phosphonopolycarboxylic acids such as 2-phosphonobutan-1,2,4-tricarboxylic acid, cyclodextrins, and alkalistannates (sodium stannate), alkalipyrophosphates (tetrasodiumpyrophosphate, disodiumpyrophosphate), alkaliphosphates (sodium phosphate), and phosphoric acid and colour-changing salts thereof.

Further Ingredients

The agents (A) as contemplated herein and/or the oxidant preparation (B) can additionally contain further active substances, auxiliaries and additives, such as cationic surfactants, amphoteric surfactants, anionic surfactants, nonionic and/or cationic polymers, structuring agents such as glucose, maleic acid and lactic acid, alkalising agents such as ammonia, monoethanolamine, potassium hydroxide and sodium hydroxide, perfume oils, fibre structure-improving active substances, in particular mono-, di- and oligosaccharides, such as glucose, galactose, fructose, fruit sugars and lactose; colourants for colouring the agent; anti-dandruff active substances, such as piroctone, olamine, zinc omadine and climbazole; amino acids and oligopeptides; animal-based and/or plant-based protein hydrolysates, and those in the form of their fatty acid condensation products or optionally anionically or cationically modified derivatives; vegetable oils; light stabilisers and UV blockers; active substances such as panthenol, pantothenic acid, pantolactone, allantoin, pyrrolidinone carboxylic acids and colour-changing salts thereof and bisabolol; polyphenols, in particular hydroxycinnamic acids, 6,7-dihydroxycoumarin, hydroxybenzoic acids, catechins, tannins, leukoanthocyanidins, anthocyanidins, flavanones, flavones and flavonols; ceramides or pseudoceramides; vitamins, pro-vitamins and vitamin precursors; plant extracts; swelling and penetrating substances such as glycerol, propylene glycol monoethyl ether, carbonates, hydrogen carbonates, guanidines, ureas and primary, secondary and tertiary phosphates; turbidity agents such as latex, styrene/PVP and styrene/acrylamide copolymers; pearlescent agents such as ethylene glycol mono- and distearate and PEG-3 distearate; pigments as well as propellants such as propane-butane mixtures, $N_2O$, dimethyl ether, $CO_2$ and air.

The additional active substances and auxiliaries are used in the agents as contemplated herein preferably in amounts of, in each case, from about 0.0001 to about 10% by weight, in particular from about 0.0005 to about 5% by weight, in relation to the total weight of the agent (A) or the oxidant preparation (B).

That said in respect of the dye agent (A) as contemplated herein applies mutatis mutandis to the preferred embodiments of the multi-component packaging unit as contemplated herein.

Method for Producing the Agent (A)

The agents (A) as contemplated herein are particularly preferably produced by a special method by which the creation of uni- and multilamellar vesicles can be ensured.

A third subject of the present disclosure is therefore a method for producing an agent (A) according to the first subject of the present disclosure, said method comprising the following steps (I) heating a mixture formed of (a1) $C_8$-$C_{30}$ fatty alcohol, (a2) ethoxylated fatty alcohol of formula (I), (a3) anionic surfactant of formula (II), and a first partial amount of water to a temperature from about 65 to about 85° C. in a first container, (II) producing a mixture formed of a second partial amount of water and the colour-changing salts from the group of sulfates, hydrogen sulfates, chlorides (a4) in a second container, (III) adding the preparation obtained in step (II) to the preparation obtained in step (I) and heated to between from about 40 and about 60° C., with constant stirring by employing a propeller agitator at a rate of at least 500 revolutions per minute, (IV) cooling the mixture obtained in step (III) with constant stirring to between from about 20 and about 40° C.

The introduction of high shear forces in step (III) of the method has proven to be particularly preferred for the production of unilamellar and multilamellar vesicles. Accordingly high shear forces can be generated for example by stirring the formulation using a propeller agitator, for example at a rate of at least 500 revolutions per minute, more preferably at a rate of 800 revolutions per minute.

It has proven to be particularly preferred if the (III) addition of the preparation obtained in step (II) to the preparation obtained in step (I) and heated to between from about 40 and about 60° C. is performed with constant stirring by employing a propeller agitator at a rate of at least 800 revolutions per minute, That said in respect of the dye agent (A) as contemplated herein and in respect of the multi-component packaging unit as contemplated herein applies mutatis mutandis to the preferred embodiments of the method as contemplated herein.

Examples

The following compositions were produced (all values in % by weight)

|  | Ex 1 | Ex 2 | Ex 3 | Ex 4 |
|---|---|---|---|---|
| Cetearyl alcohol ($C_{16}$-$C_{18}$ fatty alcohols) | 13.0 | 13.0 | 13.0 | 13.0 |
| 2-octyldodecanol | 2.0 | 2.0 | 2.0 | 2.0 |
| Ceteareth-20 | 3.0 | 3.0 | 3.0 | 3.0 |
| Sodium laureth sulfate (2 EO) | 2.0 | 2.0 | 2.0 | 2.0 |
| Glyceryl monostearate | 4.0 | 4.0 | 4.0 | 4.0 |
| Ammonia | 1.5 | 1.5 | 1.5 | 1.5 |
| p-toluene diamine, sulfate (mmol) | 0.1 (0.45) | 0.5 (2.27) | 1.0 (4.50) | 2.0 (9.0) |
| Resorcinol (mmol) | 0.05 (0.45) | 0.25 (2.27) | 0.50 (4.50) | 0.99 (9.0) |
| Water | to 100 | to 100 | to 100 | to 100 |

|  | Ex 5 | Ex 6 | Ex 7 |
|---|---|---|---|
| Cetearyl alcohol (C16-C18 fatty alcohols) | 13.0 | 13.0 | 13.0 |
| 2-octyldodecanol | 2.0 | 2.0 | 2.0 |
| Ceteareth-20 | 3.0 | 3.0 | 3.0 |
| Sodium laureth sulfate (2 EO) | 2.0 | 2.0 | 2.0 |
| Glyceryl monostearate | 4.0 | 4.0 | 4.0 |
| Ammonia | 1.5 | 1.5 | 1.5 |
| p-toluene diamine, sulfate (mmol) | 3.0 (13.6) | 4.0 (18.2) | 6.5 (29.5) |
| Resorcinol (mmol) | 1.5 (13.6) | 2.00 (18.2) | 3.24 (29.5) |
| Water | to 100 | to 100 | to 100 |

The formulations were produced as follows:

Cetearyl alcohol and 2-octyldodecanol were heated together with Ceteareth-20, sodium laureth sulfate (2EO), glyceryl monostearate and with a first partial amount of water, with stirring, to 75° C. (fat phase).

Ammonia and the oxidation dye precursors were then mixed with a second partial amount of water at 20-30° C. (dye phase).

Once the fat phase was cooled to 50° C., the dye phase heated to 30° C. was incorporated into the fat phase with stirring by employing a propeller agitator at 1000 revolutions per minute.

The formulations produced in this way were left to cool to room temperature, with stirring by employing a propeller agitator at 1000 revolutions per minute.

Once produced, all formulations were assessed in respect of their stability.

|  | Salt content (% by weight) | 24 h after production | 4 weeks after production | Stability 1 = very good 6 = very poor |
|---|---|---|---|---|
| Ex 1 | 0.1 | semi-transparent gel | gel-like, viscous | 2 |
| Ex 2 | 0.5 | semi-transparent gel | gel-like, viscous | 2 |
| Ex 3 | 1.0 | white cream | thick cream | 1 |
| Ex 4 | 2.0 | white cream | thick cream | 1 |
| Ex 5 | 3.0 | white cream | thick cream | 1 |
| Ex 6 | 4.0 | white cream | thick cream | 2 |
| Ex 7 | 6.5 | white cream | separation of droplets, phase separation, thin | 5 |

After 24 hours the formulations were examined under a polarisation microscope (Zeiss Axio Scope a2):

|  | Salts |  |
|---|---|---|
| Ex 1 | 0.1 | lamellar phase, primarily with linear, parallel structures |
| Ex 3 | 1.0 | Maltese crosses, approximately 4-5 μm (micrometres), multilamellar vesicles |
| Ex 5 | 3.0 | Maltese crosses, approximately 5-6 μm (micrometres), multilamellar vesicles |
| Ex 6 | 4.0 | Maltese crosses, approximately 7-20 μm (micrometres), multilamellar vesicles |
| Ex 7 | 6.5 | Maltese crosses, approximately 20 μm (micrometres) |

Further Formulation Examples

The following colouring creams were produced (all values in % by weight) The

|  | CC1 | CC2 | CC3 |
|---|---|---|---|
| Carbomer (polyacrylic acid, ammonium salt, homopolymer) | 0.2 | 0.2 | 0.2 |
| C16-C18 fatty alcohol sulfate, sodium salt | 0.7 | 0.7 | 0.7 |
| Sodium laureth sulfate (C12-C14 fatty alcohol, 2-3 EO) | 1.3 | 1.3 | 1.3 |
| Potassium oleate | 0.5 | 0.5 | 0.5 |
| Potassium hydroxide | 0.09 | 0.09 | 0.09 |
| EDTA, disodium salt | 0.03 | 0.03 | 0.03 |
| 2-octyldodecanol | 2.2 | 2.2 | 2.2 |
| Cetearyl alcohol (C16-C18 fatty alcohols) | 13.2 | 13.2 | 13.2 |
| Ceteareth-20 | 3.3 | 3.3 | 3.3 |
| Titanium dioxide | 0.5 | 0.5 | 0.5 |
| Merquat Plus 3330 (Polyquaternium-39), dimethyl diallyl ammonium chloride, acrylamide, acrylic acid, terpolymer | 1.5 | 1.5 | 1.5 |
| Ammonia (25% aqueous solution) | 6.0 | 6.0 | 6.0 |
| p-toluene diamine, sulfate | 3.1 | 3.5 | 2.4 |
| Resorcinol | — | 1.0 | 0.2 |
| 2-amino-3-hydroxypryridine | — | — | 0.8 |
| 2-amino-4-(hydroxyethylamino)anisole, sulfate | 1.0 | — | 1.0 |
| m-aminophenol | — | 1.7 | 0.7 |
| Water | to 100 | to 100 | to 100 |
| Maltese crosses (multilamellar vesicles) | yes | yes | yes |

|  | CC4 | CC5 | CC6 |
|---|---|---|---|
| Carbomer (polyacrylic acid, ammonium salt, homopolymer) | 0.2 | 0.2 | 0.2 |
| C16-C18 fatty alcohol sulfate, sodium salt | 0.7 | 0.7 | 0.7 |
| Sodium laureth sulfate (C12-C14 fatty alcohol, 2-3 EO) | 1.3 | 1.3 | 1.3 |
| Potassium oleate | 0.5 | 0.5 | 0.5 |
| Potassium hydroxide | 0.09 | 0.09 | 0.09 |
| EDTA, disodium salt | 0.03 | 0.03 | 0.03 |
| 2-octyldodecanol | 2.2 | 2.2 | 2.2 |
| Cetearyl alcohol (C16-C18 fatty alcohols) | 13.2 | 13.2 | 13.2 |
| Ceteareth-20 | 3.3 | 3.3 | 3.3 |
| Titanium dioxide | 0.5 | 0.5 | 0.5 |
| Merquat Plus 3330 (Polyquaternium-39), dimethyl diallyl ammonium chloride, acrylamide, acrylic acid, terpolymer | 1.5 | 1.5 | 1.5 |
| Ammonia (25% aqueous solution) | 6.0 | 6.0 | 6.0 |
| p-toluene diamine, sulfate | 2.0 | 0.5 | — |
| 2-(2-hydroxyethyl)-p-phenylenediamine sulfate | 1.1 | 2.3 | 4.1 |
| 1-naphthol | 1.8 | 2.2 | 1.6 |
| 5-amino-2-methylphenol | 0.1 | — | 1.2 |
| Water | to 100 | to 100 | to 100 |
| Maltese crosses (multilamellar vesicles) | yes | yes | yes |

|  | CC7 | CC8 | CC9 |
|---|---|---|---|
| carbomer (polyacrylic acid, ammonium salt, homopolymer) | 0.2 | 0.2 | 0.2 |
| C16-C18 fatty alcohol sulfate, sodium salt | 0.7 | 0.7 | 0.7 |
| Sodium laureth sulfate (C12-C14 fatty alcohol, 2-3 EO) | 1.3 | 1.3 | 1.3 |
| Potassium oleate | 0.5 | 0.5 | 0.5 |
| Potassium hydroxide | 0.09 | 0.09 | 0.09 |
| EDTA, disodium salt | 0.03 | 0.03 | 0.03 |
| 2-octyldodecanol | 2.2 | 2.2 | 2.2 |
| Cetearyl alcohol (C16-C18 fatty alcohols) | 13.2 | 13.2 | 13.2 |
| Ceteareth-20 | 3.3 | 3.3 | 3.3 |
| Titanium dioxide | 0.5 | 0.5 | 0.5 |
| Merquat Plus 3330 (Polyquaternium-39), dimethyl diallyl ammonium chloride, acrylamide, acrylic acid, terpolymer | 1.5 | 1.5 | 1.5 |
| Ammonia (25% aqueous solution) | 6.0 | 6.0 | 6.0 |
| 4,5-diamino-1-(2-hydroxyethyl)-1H-pyrazole sulfate | 3.4 | 3.0 | 2.9 |
| 3-amino-6-chloro-2-methylphenol | 3.1 | 0.05 | — |
| 5-amino-2-methylphenol | — | 1.5 | 1.6 |
| 2-methylresorcinol | 0.1 | 2.4 | 0.5 |
| Water | to 100 | to 100 | to 100 |
| Maltese crosses (multilamellar vesicles) | yes | yes | yes |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for changing the colour of keratin fibres, which agent comprises unilamellar vesicles and/or multilamellar vesicles having a mean diameter from about 0.02 to about 6.0 µm in an aqueous medium, and wherein the agent comprises
(a1) one or more linear, saturated $C_8$-$C_{30}$ fatty alcohols in a total amount from about 10.0 to about 18.0% by weight and one or more branched, saturated $C_{12}$-$C_{30}$ fatty alcohols in a total amount from about 1.9 to about 3.0% by weight, wherein the amounts are in relation to the total weight of the agent,
(a2) at least one ethoxylated fatty alcohol of formula (I),

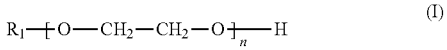
$$R_1 \!-\!\!\!-\!\!\!\left[\!O\!-\!CH_2\!-\!CH_2\!-\!O\!\right]_{\!n}\!\!\!-\!\!\!-\! H \quad (I)$$

in which
R1 stands for a linear or branched, saturated or unsaturated $C_8$-$C_{30}$ alkyl group and
n stands for an integer from about 10 to about 30,
wherein the at least one ethoxylated fatty alcohol is present in an amount of from about 1.5 to about 4.0% by weight in relation to the total weight of the agent,
(a3) at least one anionic surfactant of formula (II)

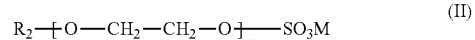
$$R_2 \!-\!\!\!-\!\!\!\left[\!O\!-\!CH_2\!-\!CH_2\!-\!O\!\right]_{\!m}\!\!\!-\!\!\!-\! SO_3M \quad (II)$$

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$), wherein the at least one anionic surfactant is present in an amount of from about 1.0 to about 3.0% by weight in relation to the total weight of the agent, and
(a4) one or more colour-changing salts chosen from the group of sulfates, hydrogen sulfates, chlorides and/or bromides in a total amount of from about 0.3 to about 6.0% by weight, wherein the total amount relates to the total weight of the agent; and water in an amount of from about 65 to about 75% by weight in relation to the total weight of the agent.

2. The agent according to claim 1, wherein the agent comprises multilamellar vesicles.

3. The agent according to claim 1, comprising:
(a31) at least one first anionic surfactant of formula (II), in which
R2 stands for a linear, saturated $C_8$-$C_{30}$ alkyl group and m stands for the number 0, and
(a32) at least one second anionic surfactant of formula (II), in which
R2 stands for a linear, saturated $C_8$-$C_{30}$ alkyl group and m stands for an integer from about 1 to about 5.

4. The agent according to claim 1, comprising (a4) one or more colour-changing salts chosen from the group of phenylenediamine sulfate, phenylenediamine monohydrochloride, phenylenediamine dihydrochloride, p-toluene diamine sulfate, p-toluene diamine monohydrochloride, p-toluene diamine dihydrochloride, 2-(2-hydroxyethyl)-p-phenylenediamine sulfate, 2-(2-hydroxyethyl)-p-phenylenediamine monohydrochloride, 2-(2-hydroxyethyl)-p-phenylenediamine dihydrochloride, N,N-bis-(2-hydroxyethyl)-p-phenylenediamine sulfate, N,N-bis-(2-hydroxyethyl)-p-phenylenediamine monohydrochloride, N,N-bis-(2-hydroxyethyl)-p-phenylenediamine dihydrochloride, 2-methoxymethyl-p-phenylenediamine sulfate, 2-methoxymethyl-p-phenylenediamine monohydrochloride, 2-methoxymethyl-p-phenylenediamine dihydrochloride, p-aminophenol hydrogen sulfate, p-aminophenol monohydrochloride, 4-amino-3-methylphenol hydrogen sulfate, 4-amino-3-methylphenol chloride, 2,4,5,6-tetraaminopyrimidine monosulfate, 2,4,5,6-tetraaminopyrimidine disulfate, 2,4,5,6-tetraaminopyrimidine monohydrochloride, 2,4,5,6-tetraaminopyrimidine dihydrochloride, 2,4,5,6-tetraaminopyrimidine trihydrochloride, 2,4,5,6-tetraaminopyrimidine tetrahydrochloride, 4-hydroxy-2,5,6-triaminopyrimidine sulfate, 4-hydroxy-2,5,6-triaminopyrimidine monohydrochloride, 4-hydroxy-2,5,6-triaminopyrimidine dihydrochloride, 4-hydroxy-2,5,6-triaminopyrimidine trihydrochloride, 4,5-diamino-1-(2-hydroxyethyl)-1H-pyrazole sulfate, 4,5-diamino-1-(2-hydroxyethyl)-1H-pyrazole monohydrochloride and/or 4,5-diamino-1-(2-hydroxyethyl)-1H-pyrazole dihydrochloride.

5. The agent according to claim 1, comprising—in relation to the total weight of the agent—(a4) one or more colour-changing salts chosen from the group of sulfates, hydrogen sulfates, chlorides and/or bromides in a total amount from about 0.5 to about 5.5% by weight.

6. The agent according to claim 1, comprising—in relation to the total weight of the agent—phosphorous compounds in a total amount of less than about 0.1% by weight.

7. The agent according to claim 1, comprising:
(A5) at least one $C_8$-$C_{30}$ fatty acid monoglyceride, a $C_8$-$C_{30}$ fatty acid diglyceride and/or a $C_8$-$C_{30}$ fatty acid triglyceride.

8. The agent according to claim 1, comprising—in relation to the total weight of the agent—(a5) one or more $C_8$-$C_{30}$ fatty acid monoglycerides in a total amount from about 1.0 to about 6.0% by weight.

9. A multi-component packaging unit for the oxidative dyeing of keratin fibres, comprising, packaged separately from one another,
a container (I) comprising a cosmetic agent (A) and
a container (II) comprising a cosmetic agent (B), wherein
the agent (A) in container (I) is a dye agent according to claim 1, and
the agent (B) in the container (II) is an oxidant preparation comprising hydrogen peroxide.

10. The agent of claim 1, wherein:
the one or more linear, saturated $C_5$-$C_{30}$ fatty alcohols (a1) comprises cetearyl alcohol, and
the one or more branched, saturated $C_{12}$-$C_{30}$ fatty alcohols (a1) comprises 2-octyldodecanol.

11. The agent according to claim 1, comprising—based on the total weight of the agent, 0.9 to about 4.5% by weight of the (a4) one or more colour-changing salts.

12. A method for producing a dye agent for changing the colour of keratin fibres, which agent comprises unilamellar vesicles and/or multilamellar vesicles in an aqueous medium, and wherein the agent comprises
(a1) at least one $C_8$-$C_{30}$ fatty alcohol,
(a2) at least one ethoxylated fatty alcohol of formula (I),

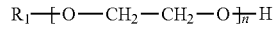

in which
R1 stands for a linear or branched, saturated or unsaturated $C_8$-$C_{30}$ alkyl group and
n stands for an integer from about 10 to about 100,
(a3) at least one anionic surfactant of formula (II)

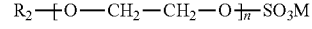

in which
R2 stands for a linear or branched, saturated or unsaturated $C_8$-$C_{30}$ alkyl group,
m stands for an integer from 0 to about 10, and
M stands for a hydrogen atom, an equivalent of a sodium ion, a potassium ion, or an ammonium ion ($NH_4^+$), and
(a4) one or more colour-changing salts chosen from the group of sulfates, hydrogen sulfates, chlorides and/or bromides in a total amount of from about 0.3 to about 6.0% by weight, wherein the total amount relates to the total weight of the agent, wherein the method comprises the following steps
(I) heating a mixture comprising (a1) at least one $C_{12}$-$C_{30}$ fatty alcohol, (a2) at least one ethoxylated fatty alcohol of formula (I), (a3) at least one anionic surfactant of formula (II), and a first partial amount of water to a temperature from about 65 to about 85° C. in a first container,
(II) producing a mixture comprising a second partial amount of water and (a4) one or more colour-changing salts chosen from the group of sulfates, hydrogen sulfates, chlorides in a second container,
(III) adding the preparation obtained in step (II) to the preparation obtained in step (I) and heating to between from about 40 and about 60° C., with constant stirring by employing a propeller agitator at a rate of at least 500 revolutions per minute,
(IV) cooling the mixture obtained in step (III) with constant stirring to between about 20 and about 40° C.

13. The method according to claim 12, wherein the agent comprises—in relation to the total weight of the agent—(a1) one or more linear, saturated $C_8$-$C_{30}$ fatty alcohols in a total amount from about 5.0 to about 25.0% by weight.

14. The method according to claim 12, wherein the agent comprises—in relation to the total weight of the agent—(a1)

one or more branched, saturated $C_{12}$-$C_{30}$ fatty alcohols in a total amount from about 1.0 to about 9.0% by weight.

15. The method according to claim 12, wherein the agent comprises (a2) at least one ethoxylated fatty alcohol of formula (I), in which R1 stands for a linear or branched, saturated or unsaturated $C_8$-$C_{30}$ alkyl group, and n stands for an integer from about 10 to about 30.

16. The method according to claim 12, wherein the agent comprises—in relation to the total weight of the agent—(a2) one or more ethoxylated fatty alcohols of formula (I) in a total amount from about 0.5 to about 5.0% by weight.

17. The method according to claim 12, wherein the agent comprises—in relation to the total weight of the agent—(a3) one or more anionic surfactants of formula (II) in a total amount from about 0.5 to about 4.8% by weight.

18. The method according to claim 12, wherein (III) addition of the preparation obtained in step (II) to the preparation obtained in step (I) and heating to between about 40 and about 60° C., with constant stirring by employing a propeller agitator is conducted with stirring at a rate of at least 800 revolutions per minute.

19. The method according to claim 12, wherein the agent comprises—in relation to the total weight of the agent:

(a1) one or more linear, saturated $C_5$-$C_{30}$ fatty alcohols in a total amount from about 12.0 to about 16.0% by weight, (a1) one or more branched, saturated $C_{12}$-$C_{30}$ fatty alcohols in a total amount from about 1.9 to about 3.0% by weight, (a2) one or more ethoxylated fatty alcohols of formula (I) in a total amount from about 2.0 to about 3.5% by weight, (a3) one or more anionic surfactants of formula (II) in a total amount from about 1.0 to about 3.0% by weight, and (a4) one or more colour-changing salts chosen from the group of sulfates, hydrogen sulfates, chlorides and/or bromides in a total amount from about 2.1 to about 3.4% by weight.

20. The agent according to claim 19, wherein the agent comprises multilamellar vesicles.

* * * * *